United States Patent [19]

Yosida

[11] Patent Number: 4,764,545

[45] Date of Patent: Aug. 16, 1988

[54] PROCESS FOR PREPARING α-CYANOACRYLATE TYPE COMPOUNDS AND ADHESIVE COMPOSITION COMPRISING α-CYANOACRYLATE TYPE COMPOUND OBTAINED BY THE PROCESS AS ITS MAIN COMPONENT

[75] Inventor: Ethuo Yosida, Kameoka, Japan

[73] Assignee: Ohara Paragium Chemical, Co., Ltd., Kyoto, Japan

[21] Appl. No.: 1,476

[22] Filed: Jan. 8, 1987

[30] Foreign Application Priority Data

Jan. 10, 1986 [JP] Japan .................. 61-4036

[51] Int. Cl.$^4$ .................. C08K 3/36; C07C 121/413
[52] U.S. Cl. .................. 523/212; 523/213; 524/850; 558/443
[58] Field of Search ............ 523/212, 213; 524/850; 558/443

[56] References Cited

U.S. PATENT DOCUMENTS

| | | | |
|---|---|---|---|
| 2,784,215 | 3/1957 | Joyner | 524/850 |
| 3,444,233 | 5/1969 | Rabinowitz | 558/443 |
| 3,896,077 | 7/1975 | Leonard et al. | 524/850 |
| 4,477,607 | 10/1984 | Litke | 523/212 |

Primary Examiner—Lewis T. Jacobs
Attorney, Agent, or Firm—Armstrong, Nikaido, Marmelstein & Kubovcik

[57] ABSTRACT

A process for preparing an α-cyanoacrylate compound characterized by the steps of thermally depolymerizing a condensation product obtained from a cyanoacetic acid ester, and formaldehyde or a polymer thereof using as a catalyst a polymerizable imine represented by the formula

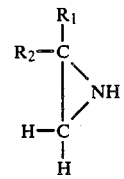

wherein $R_1$ and $R_2$ are the same or different and are each $CH_3$ or H to obtain a crude monomer, and rectifying the crude monomer and an adhesive composition comprising as its main component an α-cyanoacrylate compound prepared by the above process.

4 Claims, No Drawings

PROCESS FOR PREPARING α-CYANOACRYLATE TYPE COMPOUNDS AND ADHESIVE COMPOSITION COMPRISING α-CYANOACRYLATE TYPE COMPOUND OBTAINED BY THE PROCESS AS ITS MAIN COMPONENT

The present invention relates to a novel process for preparing high-purity α-cyanoacrylate compounds and to adhesive compositions comprising a high-purity α-cyanoacrylate compound obtained by the process as the main component and preferably containing finely divided silica surface-treated with a siliceous compound as a thixotropic agent.

Adhesive compositions consisting primarily of an α-cyanoacrylate are widely used for immediately giving adhesive bonds. Examples of α-cyanoacrylates for such compositions are alkyl-α-cyanoacrylates such as methyl-α-cyanoacrylate, ethyl-α-cyanoacrylate, i-butyl-α-cyanoacrylate, n-butyl-α-cyanoacrylate and n-propyl-α-cyanoacrylate; α-cyanoacrylates having an unsaturated group, such as allyl-α-cyanoacrylate and propargyl-α-cyanoacrylate; α-cyanoacrylates having alkoxyl, such as 2-methoxyethyl-α-cyanoacrylate and 2-ethoxyethyl-α-cyanoacrylate; and special α-cyanoacrylates such as alkyloxyalkyl-α-cyanoacrylates and tetrahydrofurfuryl-α-cyanoacrylate.

Such α-cyanoacrylates have heretofore been produced industrially usually by a process comprising the steps of reacting a cyanoacetate with formaldehyde or a polymer thereof in an inert organic solvent in the presence of a basic catalyst to obtain a condensation product, azeotropically removing the resulting water along with the solvent, subsequently removing the remaining solvent by distillation, thereafter thermally depolymerizing the condensation product in a vacuum in the presence of a nonvolatile acid such as phosphorus pentoxide to obtain a crude α-cyanoacrylate and rectifying the crude product. The basic catalysts to be used for this process are usually nonpolymerizable basic compounds, such as piperidine and like amines, sodium hydroxide, potassium hydroxide and alkoxides of alkali metals, such that the catalyst remains free of polymerization even when acted on by an acid or heat.

When the α-cyanoacrylate produced by the conventional process is used for preparing an adhesive composition as its main component, the composition has the following drawbacks even when incorporating a suitable stabilizer. (1) The setting time greatly extends with the lapse of time during storage. (2) When incorporating other ingredients such as thixotropic agent, tackifier, etc. for improving other properties, the composition exhibits impaired storage stability.

For example, thixotropic adhesive compositions have incorporated therein finely divided hydrophobic silica which is prepared by treating fine particles of silica with a siliceous compound to replace the hydroxyl groups covering the particles by organic hydrophobic groups, or finely divided oleophilic silica which is prepared by treating fine particles of silica with a silane compound having a functional group to replace the surface hydroxyl groups by functional oleophilic groups. Further a tackifier such as polymethyl methacrylate or methacrylic copolymer is used for preparing a highly viscous adhesive composition. These compositions have the drawback of low storage stability. Accordingly, when an increased amount of stabilizer is added to the composition so as to enable the composition to retain useful storage stability, the composition requires an increased setting time. Especially when heated, for example, when allowed to stand in a constant-temperature chamber at 70°±2° C. as in the usual storage stability test, the composition thereafter requires a greatly extended setting time, consequently failing to give adhesive bonds immediately. Thus, short setting time, which is the greatest requirement for the adhesive compositions of the type described, must be sacrificed. The use of the α-cyanoacrylate produced by the conventional process therefore entails various problems.

The above drawbacks are attributable to the conventional process in which the condensation step is followed by the decomposition step to obtain a monomer again and which invariably permits presence of various impurities which are almost unremovable.

An object of the present invention is to provide a high-purity α-cyanoacrylate compound (hereinafter referred to merely as "α-cyanoacrylate type compound") which is usable as the main component of adhesive compositions without entailing the foregoing drawbacks of the conventional α-cyanoacrylate.

Another object of the present invention is to provide a process for preparing an α-cyanoacrylate type compound free of the drawbacks of the conventional α-cyanoacrylate.

Another object of the present invention is to provide an adhesive composition comprising as its main component an α-cyanoacrylate type compound free of the foregoing drawbacks of the conventional α-cyanoacrylate.

Stated more specifically, it is an object of the present invention to develop an α-cyanoacrylate type compound having such outstanding characteristics as to afford an adhesive composition which has outstanding storage stability and remains unchanged in setting time despite the lapse of time and which retains its properties even when incorporating other components and also to develop such an excellent adhesive composition free of the foregoing drawbacks.

These objects can be achieved by preparing an α-cyanoacrylate type compound by an entirely novel process instead of the conventional process and by using the α-cyanacrylate type compound for preparing an adhesive composition as its main component, more particularly by using a polymerizable catalyst in place of the basic catalyst which is used in the conventional α-cyanoacrylate preparing process and not polymerizable even when subjected to the action of heat or acids, more preferably by using the new catalyst and using the specified distillation column to be described below for depolymerization and/or rectification.

Stated more specifically, the present invention provides a process for preparing an α-cyanoacrylate type compound characterized by thermally depolymerizing a condensation product obtained from a cyanoacetic acid ester, and formaldehyde or a polymer thereof using as a catalyst a polymerizable imine represented by the formula

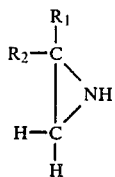

(I)

wherein $R_1$ and $R_2$ are the same or different and are each $CH_3$ or H to obtain a crude monomer, and rectifying the crude monomer. The invention further provides an adhesive composition comprising the α-cyanoacrylate type compound thus prepared as its main component.

The process of the present invention for preparing α-cyanoacrylate type compounds comprises the steps of condensation, depolymerization and rectification. The process is distinctly characterized by (1) using a strongly basic compound, such as ethyleneimine or 2,2-dimethylethyleneimine, which is polymerizable by an acid and/or heat as a condensing catalyst for obtaining a condensation product from a cyanoacetate and formaldehyde in preparing the α-cyanoacrylate (hereinafter referred to as "monomer") type compound, and further preferably by (2) using the above catalyst and using for the depolymerization step and/or the rectification step a distillation column accommodating a plurality of containers packed with a mixture of phosphorus pentoxide (hereinafter abbreviated as "$P_2O_5$") and hydroquinone (hereinafter abbreviated as "HQ"), the container being adapted to permit the monomer type compound or vapor thereof to come into contact with the mixture.

When the monomer type compound contemplated by the present invention and prepared by the specified process is used for preparing an adhesive composition as its main component, the composition obained has the advantages of being excellent in storage stability, remaining unchanged in setting time despite the lapse of time, and retaining these properties even when incorporating other components, as will become apparent from the examples given later, although the reason has yet to be fully clarified.

In practicing the process of the present invention, a cyanoacetate is first reacted with formaldehyde or a polymer thereof in an amount of 0.8 to 1.2 moles, preferably 0.96 to 1.05 moles, per mole of the cyanoacetate in an inert solvent capable of forming an azeotrope with water or codistilling with water, such as alcohol, benzene, toluene or trichloroethylene, in the presence of a polymerizable imine represented by the formula (I), such as ethyleneimine or 2,2-dimethylethyleneimine, in an amount of 0.01 to 3 mole %, preferably 0.015 to 0.3 mole %, based on the cyanoacetate to obtain a condensation product. The solvent is used preferably in an amount of 60 to 200 ml per mole of the cyanoacetate. The condensation reaction is carried out at a temperature of 30° to 150° C., preferably at a refluxing temperature of 70° to 100° C. Suitably the reaction time is 30 minutes to 15 hours. The cyanoacetate to be used is any of those heretofore used for preparing α-cyanoacrylates. The formaldehyde to be used is not limited to formaldehyde only, but a polymer is usually about 8 to about 100 in the degree of polymerization.

On completion of the condensation reaction, $H_2SO_4$, $H_3PO_4$, p-toluenesulfonic acid, 2-hydroxy-4-methoxybenzophenone-5-sulfonic acid or like acids is added to the reaction mixture in an amount of 1.2 to 5 moles, preferably 1.5 to 3.0 moles, per mole of the imine to catalytically inactivate the imine (which has been polymerized as by heat). The water resulting from the reaction is thereafter azeotropically removed from the reaction mixture, and the remaining solvent is then distilled off.

Subsequently, the condensation product is heated at a temperature of 100° to 130° C., preferably 110° to 120° C., in a vacuum of up to 3 mm Hg for 10 minutes to several hours, preferably for 30 minutes to 2 hours, to completely remove low-boiling fractions from the product.

Next, with 2 to 3 wt. % of $P_2O_5$ and 1 to 2 wt. % of HQ uniformly admixed with the condensation product, the product is depolymerized at a temperature of 140° to 250° C., preferably 150° to 190° C., in a vacuum of up to 3 mm Hg to obtain a crude monomer.

Subsequently, with addition of 1 to 2 wt. % of each of $P_2O_5$ and HQ preferably along with 0.001 to 0.25 wt. % of an acid, such as 2-hydrox-4-methoxybenzophenone-5-sulfonic acid, based on the crude monomer obtained by depolymerization, the monomer is rectified in a vacuum of up to 2 mm Hg to obtain the desired monomer type compound.

It is especially desirable to use the below-specified distillation column for the depolymerization step and/or the rectification step of the process of the invention. The distillation column is packed with a plurality of packages each prepared by filling a mixture of $p_2O_5$ and HQ usually in the $P_2O_5$ to HQ ratio of 1:9 to 10:0 (by weight) into a container which is adapted to bring the mixture into contact with the monomer, especially the vapor thereof. Thus, the mixture-filled packages are used as packed in the distillation column. The container to be filled with the mixture must be so constructed as to effect full contact between the mixture and the monomer, especially the monomer in the form of a vapor. The construction of the container is not limited specifically insofar as full contact is assured. Typically, for example, the container is made of a wall having a multiplicity of small holes. Such containers are packed into the distillation column suitably in accordance with the size of the column to be used and other production conditions.

The monomer type compound obtained by the present invention has a basic skeleton represented by the formula (II)

(II)

wherein R is straight-chain or branched alkyl having 1 to 16 carbon atoms or phenyl having or not having a substituent. Stated more specifically, the alkyl in the formula (I) may be one substituted with a halogen atom of alkoxy group. The phenyl may have at least one substituent such as a halogen atom or alkoxy group.

Whereas the monomer type compounds of the present invention have higher stability than the α-cyanoacrylates prepared by the prior art, α-cyanoacrylates are highly active compounds which are liable to anionic polymerization even in the presence of weak anions, for example, of a very small amount of water in the atmosphere as is well known. Accordingly, it is desirable to admix an anionic polymerization inhibitor with the monomer type compound for use as an adhesive. The monomer type compound is conjointly used with at least one anionic polymerization inhibitor such as SO₂, SO₃, NO, NO₂, HCl, H₃PO₄, aromatic sulfonic acid or alkylsulfonic acid, and/or at least one radical polymerization inhibitor such as HQ, benzoquinone, catechol, pyrogallol, hydroquinone monoethyl ether or 2-hydroxybenzoquinone, as admixed with the compound.

While the amount of polymerization inhibitor to be used somewhat varies with the type of inhibitor, usually 1 to 500 ppm, preferably 5 to 100 ppm, of the anionic polymerization inhibitor is used. The radical polymerization inhibitor is used in an amount of 1 to 2000 ppm, preferably 10 to 1200 ppm.

The monomer type compound of the present invention as stabilized with the anionic polymerization inhibitor and/or the radical polymerization inhibitor is usable as an adhesive of low viscosity exhibiting higher performance than the α-cyanoacrylate (incorporating a suitable stabilizer) available by the prior art. The present compound is usable for wider applications when other ingredients are further admixed therewith to improve the properties of the compound.

Such other ingredients to be used in formulating high-viscosity adhesive compositions with use of the present monomer type compound include a tackifier such as polymethyl methacrylate, methacrylic copolymer, cellulose acetate or like organic polymer. The organic polymer is used in such an amount as to give a viscosity usually of 10 to 5000 cps, preferably 30 to 2000 cps, although the amount is variable according to the application of the adhesive composition or the degree of polymerization of the polymer.

The monomer type compound of the present invention can be formulated also into a thixotropic pasty adhesive composition which is convenient to use and which has incorporated therein a thixotropic agent such as finely divided hydrophobic silica prepared by treating fine particles of hydrophilic silica covered with hydroxyl groups over their surfaces, with a siliceous compound such as polydimethylsiloxane, trialkoxyalkylsilane or dimethyldichlorosilane to replace the hydroxyl groups by hydrophobic groups. Another example of useful thixotropic agent is finely divided oleophilic silica which is prepared by surface-treating the hydrophilic silica with γ-methacryloxypropyltrimethoxysilane or the like to replace the surface hydroxyl groups by oleophilic methacryloxypropylsiloxyl groups. The thixotropic agent is used in an amount of 0.5 to 12 wt. %, preferably 3 to 8 wt. %, based on the present monomer type compound. The composition obtained has higher storage stability than the α-cyanoacrylate produced by the prior art, remains almost unchanged in setting time during storage despite the lapse of time and retains the features afforded by the present invention.

The present invention will be described in greater detail with reference to the following examples, in which the parts and percentages are all by weight. The properties were determined by the following methods.

Setting time

An O-ring made of NBR and 6.2 mm in diameter is cut vertically by a cutter, the specimen is applied to one of the cut surfaces, the cut ends are joined together, and the joint is forcibly pulled with both hands upon lapse of a predetermined period of time to separate the joint. The same procedure is repeated varying the separating time with an increment of 5 seconds to determine the time required for the joint to become no longer separable, as the setting time.

Storage stability

The specimen (2 to 3 g portions as contained in an aluminum tube and a polyethylene tube) is allowed to stand in a constant-temperature chamber at 70°±2° C. and checked for changes with time for 10 days. If no change occurs with reference to a blank, it is considered that the specimen will remain stable for at least one year at room temperature.

Tensile shear strength

Measured according to JIS K 6861, Item 6, using Autograph S-200, product of Shimadzu Seisakusho, Ltd.

EXAMPLE 1

Preparation of ethyl-α-cyanoacrylate type compound para-Formaldehyde (3083 parts, 86% in purity) and 6100 parts of benzole were placed into a 35-liter reactor of the steam heating type made of Hastelloy, pressurizable to a jacket pressure of up to 12 atm. and equipped with a material feeder, thermometer, efficient mechanical stirrer and reflux condenser having a water separator. The mixture was heated to 50° C. with stirring, whereupon 34 parts of 2,2-dimethylethyleneimine was added. Heating was discontinued when the benzole started reflux, and 10000 parts of ethyl cyanoacetate (99.5% in purity) was added dropwise to the mixture over a period of 25 to 30 minutes. To the mixture was thereafter added 1200 parts of tricresyl phosphate (TCP), and the mixture was subjected to condensation reaction for 30 minutes while refluxing the benzole again with heating. During this operation, the condensation water was removed as formed by means of a water separation.

After water removal was complete, 208.5 parts of 2-hydroxy-4-methoxy-benzophenone-5-sulfonic acid was added to the reaction mixture, and the mixture was thereafter heated to 110° to 115° C. to distill off a major portion of the benzole. Next, trace amounts of water and solvent and like low-boiling fractions remaining in the condensation product were completely removed in a vacuum of up to 3 mm Hg.

The condenser having the water separator was then removed and replaced by a condensor for condensing the crude monomer fraction to be obtained from depolymerization reaction. With the addition of 250 parts of P₂O₅ and 150 parts of HQ to the condensation product within the reactor, the product was heated at 150° to 185° C. in a vacuum of up to 3 mm Hg for depolymerization, giving a crude monomer.

Subsequently, the crude monomer was transferred to a vacuum distillation apparatus made of Hastelloy and equipped with an efficient mechanical stirrer, condenser, thermometer, receptacle and rectification column having the construction to be described below. With addition of 2% of P₂O₅, 1% of HQ and 0.02 to 0.22% of 2-hydroxy-4-methoxy-benzophenone-5-sulfonic acid based on the crude monomer, the monomer was rectified in a vacuum of up to 2 mm Hg to obtain 7360 parts of an ethyl-α-cyanoacrylate type compound.

The rectification column used was 90 to 92 mm in inside diameter and 500 mm in height and was packed with 15 to 25 containers having a closure, measuring 35 to 40 mm in inside diameter and 35 to 45 mm in height and made of à 30- to 40-mesh net of Hastelloy (or stainless steel). Each container was filled with a mixture of $P_2O_5$ and HQ in the ratio of 2:1.

EXAMPLE 2

Preparation of methyl-α-cyanoacrylate type compound

Into the same reactor as used in Example 1 were placed 3230 parts of p-formaldehyde (91.7% in purity), 7600 parts of methanol and 27 parts of ethyleneimine, which were then slowly heated with stirring over a period of 35 to 40 minutes until the methanol was refluxed. When the p-formaldehyde dissolved completely, heating was discontinued, whereupon 10000 parts of methyl cyanoacetate (99.5% in purity) was added dropwise to the mixture within a period of 20 minutes while suitably cooling the reactor with water. With addition of 2000 to 2200 parts of TCP, the mixture was thereafter subjected to condensation reaction for 30 to 90 minutes.

To the resulting condensation product was added 291 parts of 2-hydroxy-4-methoxy-benzophenone-5-sulfonic acid, and the mixture was heated to 110° C. to distill off a major portion of the methanol. Subsequently, with addition of 6600 parts of benzole, the water resulting from the reaction was azeotropically removed, and a major portion of the benzole was thereafter distilled off at a temperature of up to 120° C. The mixture was then maintained at 115° to 120° C. in a vacuum of up to 3 mm Hg for 30 to 120 minutes to completely remove lowboiling fractions. The same procedure as in Example 1 thereafter followed to give 7060 parts of a methyl-α-cyanoacrylate type compound.

EXAMPLE 3

Preparation of 2-methoxyisopropyl-α-cyanoacrylate type compound

Into the same reactor as used in Example 1 were placed 2270 parts of p-formaldehyde (80.05% in purity), 5500 parts of benzole and 35.5 parts of 2,2-dimethylethyleneimine, which were heated with stirring until the benzole was refluxed. After maintaining the mixture under reflux for 30 to 40 minutes, 10000 parts of 2-methoxyisopropyl cyanoacetate (99.2% in purity) was added dropwise thereto over a period of 20 to 25 minutes, followed by reaction for 60 to 90 minutes while refluxing the benzole. The water resulting from the reaction was azeotropically removed along with the benzole. Subsequently, a major portion of the benzole was distilled off at 115° to 120° C., the condensation product was then cooled to a temperature of up to 100° C., and a solution of 249 parts of 2-hydroxy-4-methoxybenzophenone-5-sulfonic acid in a mixture of 200 parts of water and 400 parts of methanol was thereafter added to the product. The mixture was maintained at a temperature of 90° to 100° C. in a vacuum of about 100 mm Hg to remove major portions of the methanol and water. The mixture was then maintained at 115° to 120° C. in a vacuum of up to 3 mm Hg for 60 to 120 minutes to completely remove the water and other low-boiling fractions from the condensation product.

The same procedure as in Example 1 thereafter followed except that the product was depolymerized at 155° to 190° C., giving 6350 parts of 2-methoxyisopropyl-α-cyanoacrylate type compound.

EXAMPLE 4

The additives and stabilizers listed in Table 1 were admixed in specified ratios with the α-cyanoacrylate type compounds prepared above by the process of the invention to obtain adhesive compositions, which were then tested for various properties. Table 1 shows the results.

For comparison, α-cyanoacrylates were prepared according to the prior art using piperidine as a condensing catalyst for cyanoacetates and p-formaldehyde without using the column of the invention. Compositions similar to those listed in Table 1 were prepared using the products and tested. Table 2 shows the results.

TABLE 1

Adhering properties of α-cyanoacrylate type compounds of Examples 1-3

| | Components of adhesive composition | | | Initial properties | | After storage stability test at 70° C. for 10 days | | |
|---|---|---|---|---|---|---|---|---|
| | α-Cyanoacrylate type compound (%) | Stabilizer (ppm) | Additive (%) | Setting time (sec) | Tensile shear strength (kg/cm$^2$) | Setting time (sec) | Tensile shear strength (kg/cm$^2$) | Stability |
| Ethyl ester type | 100 | SO$_2$:20~HQ:200 | — | 5 | 137 | 5 | 141 | Good |
| | 95 | SO$_2$:30~HQ:700 | P-MMA:5 | 15 | 144 | 20 | 142 | " |
| | 95 | SO$_2$:35~HQ:700 | RY-200:5 | 15 | 131 | 20 | 140 | " |
| | 95 | SO$_2$:30~HQ:700 | R-972:5 | 25 | 139 | 45 | 144 | " |
| | 95 | SO$_2$:35~HQ:1200 | RM-200:5 | 20 | 305 | 30 | 283 | " |
| Methyl ester type | 100 | SO$_2$:40~HQ:200 | — | 10 | 206 | 15 | 197 | Good |
| | 96 | SO$_2$:40~HQ:500 | P-MMA:4 | 20 | 215 | 30 | 210 | " |
| | 95 | SO$_2$:45~HQ:700 | RY-200:5 | 25 | 209 | 30 | 193 | " |
| | 95 | SO$_2$:40~HQ:700 | R-972:5 | 30 | 173 | 45 | 185 | " |
| | 95 | SO$_2$:40~HQ:1300 | RM-200:5 | 20 | 314 | 25 | 309 | " |
| 2-Methoxyisopropyl ester type | 100 | SO$_2$:20~HQ:100 | — | 20 | 127 | 30 | 128 | Good |
| | 96.5 | SO$_2$:30~HQ:500 | P-MMA:3.5 | 25 | 132 | 30 | 130 | " |
| | 95 | SO$_2$:30~HQ:500 | RY-200:5 | 25 | 135 | 45 | 121 | " |
| | 95 | SO$_2$:25~HQ:500 | R-972:5 | 35 | 110 | 60 | 92 | " |
| | 95 | SO$_2$:35~HQ:700 | RM-200:5 | 30 | 168 | 40 | 174 | " |

TABLE 2

Adhering properties of comparative α-cyanoacrylates prepared by conventional process

| | Components of adhesive composition | | | Initial properties | | After storage stability test at 70° C. for 10 days | | |
|---|---|---|---|---|---|---|---|---|
| | α-Cyanoacrylate type compound (%) | Stabilizer (ppm) | Additive (%) | Setting time (sec) | Tensile shear strength (kg/cm²) | Setting time (sec) | Tensile shear strength (kg/cm²) | Stability |
| Ethyl ester | 100 | SO₂:20~HQ:200 | — | 10 | 135 | 40 | 138 | Good |
| | 95 | SO₂:30~HQ:700 | P-MMA:5 | 20 | 140 | 90 | 145 | Slightly tacky |
| | 95 | SO₂:35~HQ:700 | RY-200:5 | 25 | 135 | — | — | Gelled |
| | 95 | SO₂:30~HQ:700 | R-972:5 | 30 | 126 | — | — | Tacky |
| | 95 | SO₂:35~HQ:1200 | RM-200:5 | 20 | 293 | — | — | Gelled |
| Methyl ester | 100 | SO₂:40~HQ:200 | — | 15 | 209 | 45 | 202 | Good |
| | 96 | SO₂:40~HQ:500 | P-MMA:4 | 25 | 210 | 80 | 185 | Slightly tacky |
| | 95 | SO₂:45~HQ:700 | RY-200:5 | 40 | 186 | — | — | Gelled |
| | 95 | SO₂:40~HQ:700 | R-972:5 | 60 | 177 | — | — | Gelled |
| | 95 | SO₂:40~HQ:1300 | RM-200:5 | 35 | 300 | — | — | Gelled |
| 2-Methoxyisopropyl ester | 100 | SO₂:20~HQ:100 | — | 20 | 120 | 50 | 132 | Good |
| | 96.5 | SO₂:30~HQ:500 | P-MMA:3.5 | 30 | 135 | — | — | Tacky |
| | 95 | SO₂:30~HQ:500 | RY-200:5 | 35 | 115 | — | — | Gelled |
| | 95 | SO₂:25~HQ:500 | R-972:5 | 60 | 123 | — | — | Tacky |
| | 95 | SO₂:35~HQ:700 | RM-200:5 | 45 | 160 | — | — | Gelled |

The symbols in the tables represent the following.
SO₂: sulfur dioxide
HQ: hydroquinone
P-MMA: polymethyl methacrylate
RY-200: finely divided silica surface-treated with polydimethylsiloxane (product of Nihon Aerosil Co., Ltd.)
R-972: finely divided silica surface-treated with dimethyldichlorosilane (product of Nihon Aerosil Co., Ltd.)
RM-200: finely divided silica surface-treated with γ-methacryloxypropyltrimethoxysilane (product of Nihon Aerosil Co., Ltd.)

What is claimed is:

1. A process for preparing an α-cyanoacrylate compound characterized by the steps of thermally depolymerizing a condensation product obtained from a cyanoacetic acid ester and formaldehyde or a polymer thereof, using as a catalyst a polymerizable imine represented by the formula

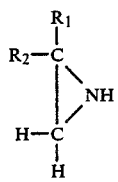

wherein R₁ and R₂ are the same or different and are each CH₃ or H to obtain a crude monomer, and rectifying the crude monomer.

2. A process as defined in claim 1 wherein a distillation column packed with a plurality of containers each filled with a mixture of phosphorus pentoxide and hydroquinone is used in the thermal depolymerizing step and/or the rectifying step, said containers being adapted to permit the mixture to contact the monomer.

3. An adhesive composition comprising as its main component an α-cyanoacrylate compound prepared by thermally depolymerizing a condensation product obtained from a cyanoacetic acid ester and formaldehyde or a polymer thereof, using as a catalyst a polymerizable imine represented by the formula

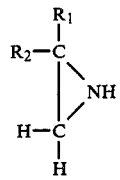

wherein R₁ and R are the same or different and are each CH₃ or H to obtain a crude monomer, and rectifying the crude monomer using a distillation column packed with a plurality of containers each filled with a mixture of phosphorus pentoxide and hydroquinone, said containers being adapted to permit the mixture to contact the monomer.

4. An adhesive composition as defined in claim 3 further comprising finely divided silica surface-treated with a siliceous compound.

* * * * *